(12) United States Patent
Cao et al.

(10) Patent No.: US 10,945,688 B2
(45) Date of Patent: *Mar. 16, 2021

(54) X-RAY IMAGING SYSTEM AND A METHOD OF X-RAY IMAGING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/177,698

(22) Filed: Nov. 1, 2018

(65) Prior Publication Data

US 2019/0069859 A1 Mar. 7, 2019

Related U.S. Application Data

(63) Continuation of application No. PCT/CN2016/108499, filed on Dec. 5, 2016.

(51) Int. Cl.
*G01T 1/167* (2006.01)
*A61B 6/00* (2006.01)
*A61B 6/03* (2006.01)
*G01V 5/00* (2006.01)
(Continued)

(52) U.S. Cl.
CPC .......... *A61B 6/4266* (2013.01); *A61B 6/032* (2013.01); *A61B 6/4233* (2013.01); *A61B 6/4241* (2013.01); *G01T 1/2018* (2013.01);
*G01T 1/24* (2013.01); *G01V 5/0016* (2013.01); *G01V 5/0025* (2013.01)

(58) Field of Classification Search
CPC ....... G01T 1/2018; G01T 1/24; G01T 1/2928; H04N 5/32

See application file for complete search history.

(56) References Cited

U.S. PATENT DOCUMENTS 4,394,676 A * 7/1983 Agouridis ............ H01L 31/115
257/429
2003/0095631 A1* 5/2003 Rosner .................. G01N 23/02
378/98.12

(Continued)

FOREIGN PATENT DOCUMENTS

CN 102448376 A 5/2012
CN 102551781 A 7/2012
(Continued)

*Primary Examiner* — David P Porta
*Assistant Examiner* — Mamadou Faye
(74) *Attorney, Agent, or Firm* — IPro, PLLC; Qian Gu

(57) ABSTRACT

Disclosed herein is an X-ray imaging system suitable for detecting x-ray, comprising: a first X-ray detector, and a second X-ray detector; wherein the first X-ray detector is configured to move relative to the second X-ray detector; wherein a spatial resolution of the first X-ray detector is higher than a spatial resolution of the second X-ray detector; wherein a detection area of the first X-ray detector is smaller than a detection area of the second X-ray detector. Also described herein is a method of X-ray imaging using the X-ray imaging system.

33 Claims, 16 Drawing Sheets

(51) Int. Cl.
*G01T 1/20* (2006.01)
*G01T 1/24* (2006.01)

(56) References Cited

U.S. PATENT DOCUMENTS

| | | | |
|---|---|---|---|
| 2004/0190676 A1* | 9/2004 | Kojima | G01N 23/046 378/19 |
| 2005/0084073 A1* | 4/2005 | Seppi | A61B 6/032 378/156 |
| 2005/0117696 A1* | 6/2005 | Suzuki | A61B 6/04 378/19 |
| 2005/0169426 A1 | 8/2005 | Groh et al. | |
| 2007/0280409 A1* | 12/2007 | Konno | A61B 6/032 378/19 |
| 2012/0057670 A1 | 3/2012 | Luhta et al. | |
| 2012/0281812 A1 | 11/2012 | Noda | |
| 2012/0307967 A1* | 12/2012 | Smith | G01V 5/0016 378/57 |
| 2014/0334600 A1* | 11/2014 | Lee | G01N 23/04 378/62 |
| 2015/0119704 A1* | 4/2015 | Roth | G01T 1/1603 600/425 |
| 2015/0177393 A1* | 6/2015 | Kovalski | A61B 6/037 250/362 |
| 2016/0099282 A1* | 4/2016 | Vora | H01L 27/14663 257/428 |
| 2017/0098757 A1* | 4/2017 | Heiba | H01L 41/0933 |
| 2017/0350990 A1* | 12/2017 | Chmeissani Raad | G01T 1/246 |
| 2020/0150288 A1* | 5/2020 | Cao | A61B 6/4266 |

FOREIGN PATENT DOCUMENTS

| | | |
|---|---|---|
| CN | 104066376 A | 9/2014 |
| CN | 105769234 A | 7/2016 |
| DE | 102012203291 A1 | 3/2013 |
| WO | 2016161542 A1 | 10/2016 |
| WO | 2016161544 A1 | 10/2016 |

* cited by examiner

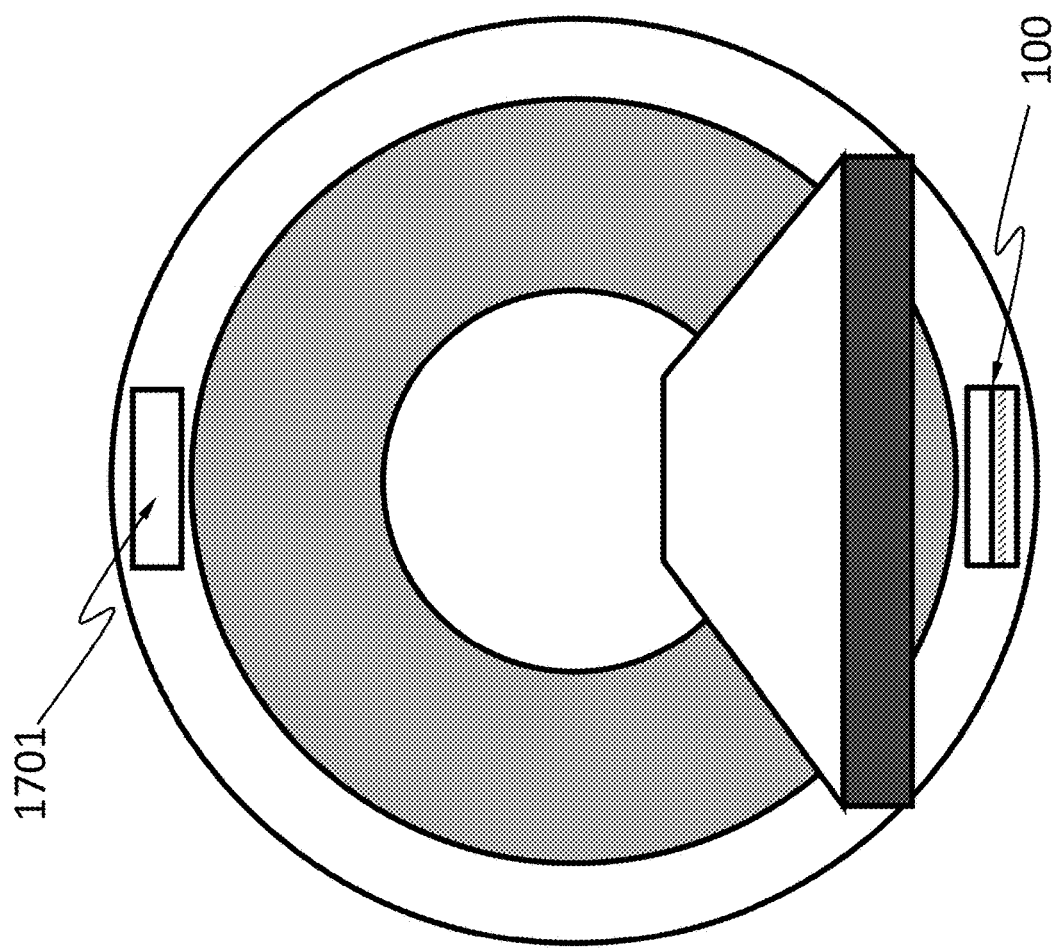

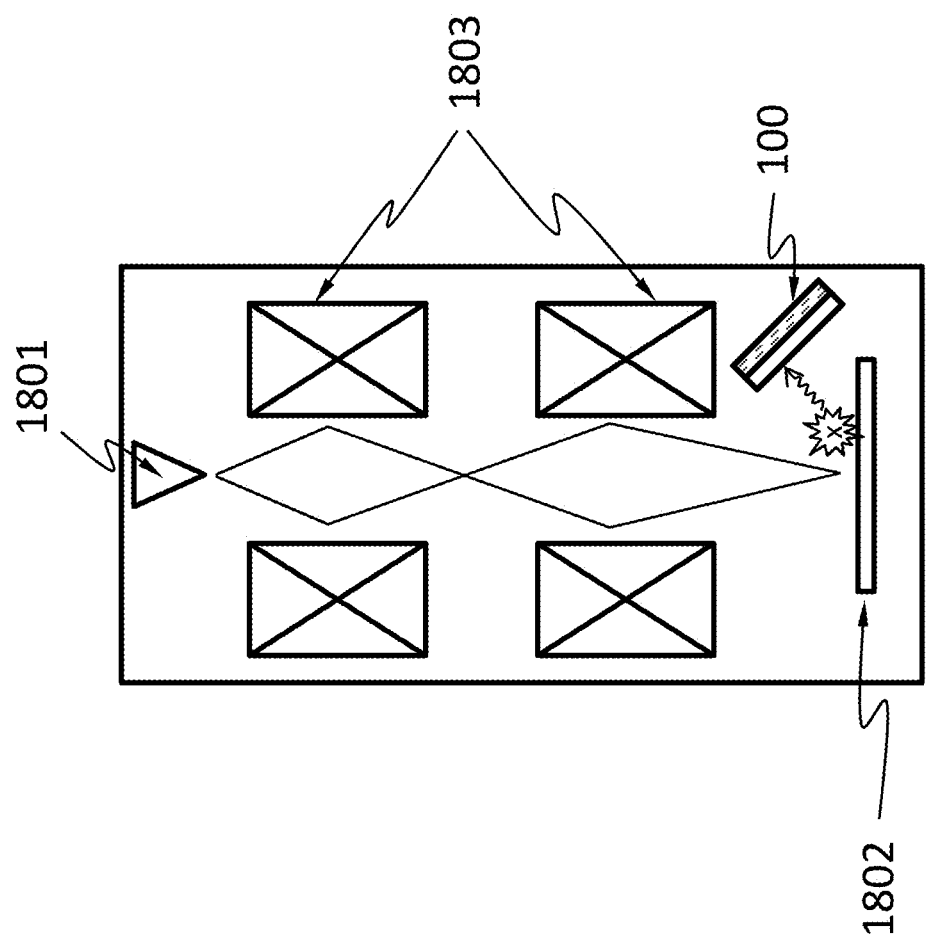

X-RAY IMAGING SYSTEM AND A METHOD OF X-RAY IMAGING

TECHNICAL FIELD

The disclosure herein relates to an X-ray imaging system and a method of X-ray imaging.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., do not require post-exposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is an X-ray imaging system suitable for detecting x-ray, comprising: a first X-ray detector, and a second X-ray detector; wherein the first X-ray detector is configured to move relative to the second X-ray detector; wherein a spatial resolution of the first X-ray detector is higher than a spatial resolution of the second X-ray detector; wherein a detection area of the first X-ray detector is smaller than a detection area of the second X-ray detector. The first X-ray detector is configured to be positioned between a source of X-ray and the second X-ray detector.

According to an embodiment, the first X-ray detector and the second X-ray detector are each capable of forming an image.

According to an embodiment, the first X-ray detector is configured to count photons of X-ray incident thereon.

According to an embodiment, the first X-ray detector is pixelated.

According to an embodiment, the first X-ray detector comprises cadmium telluride (CdTe) or cadmium zinc telluride (CZT).

The According to an embodiment, the second X-ray detector comprises a scintillator.

According to an embodiment, the X-ray detector further comprises an actuator configured to move the first X-ray detector relative to the second X-ray detector in one or more directions; wherein one of the one or more directions is not perpendicular to an imaging plane of the second X-ray detector.

According to an embodiment, the actuator comprises a material that is selected from a group consisting of aluminum, aluminum composite, carbon fiber and a combination thereof.

According to an embodiment, the actuator comprises a robotic arm.

According to an embodiment, the actuator comprises a first rail and a second rail; wherein the first X-ray detector is configured to slide along the first rail; and wherein the first rail is configured to slide along the second rail, wherein the first and second rails are not parallel.

According to an embodiment, the first X-ray detector comprises: an X-ray absorption layer comprising an electrode; a first voltage comparator configured to compare a voltage of the electrode to a first threshold; a second voltage comparator configured to compare the voltage to a second threshold; a counter configured to register a number of X-ray photons absorbed by the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the first X-ray detector further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the first X-ray detector further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

According to an embodiment, the X-ray absorption layer comprises silicon, germanium, GaAs, CdTe, CdZnTe, or a combination thereof.

According to an embodiment, the first X-ray detector does not comprise a scintillator.

According to an embodiment, disclosed herein is a system comprising an X-ray imaging system described above and an X-ray source, wherein the system is configured to perform X-ray radiography on human chest or abdomen.

According to an embodiment, the system comprises the X-ray imaging system described above and an X-ray source, wherein the system is configured to perform X-ray radiography on human mouth.

Disclosed herein is a cargo scanning or non-intrusive inspection (NII) system, comprising the X-ray imaging system described above and an X-ray source, wherein the cargo scanning or non-intrusive inspection (NII) system is configured to form an image using backscattered X-ray.

Disclosed herein is a cargo scanning or non-intrusive inspection (NII) system, comprising the X-ray imaging system described above and an X-ray source, wherein the cargo scanning or non-intrusive inspection (NII) system is configured to form an image using X-ray transmitted through an object inspected.

Disclosed herein is a full-body scanner system comprising the X-ray imaging system described above and an X-ray source.

Disclosed herein is an X-ray computed tomography (X-ray CT) system comprising the X-ray imaging system described above and an X-ray source.

Disclosed herein is an electron microscope comprising the X-ray imaging system described above, an electron source and an electronic optical system.

Disclosed herein is a system comprising the X-ray imaging system described above, wherein the system is an X-ray telescope, or an X-ray microscopy, or wherein the system is configured to perform mammography, industrial defect detection, microradiography, casting inspection, weld inspection, or digital subtraction angiography.

Described herein is a method of using an X-ray imaging system, wherein the X-ray imaging system comprises: a first X-ray detector, and a second X-ray detector; wherein the first X-ray detector is configured to move relative to the second X-ray detector; wherein a spatial resolution of the first X-ray detector is higher than a spatial resolution of the second X-ray detector; wherein a detection area of the first X-ray detector is smaller than a detection area of the second X-ray detector; wherein the method comprises: taking a first image of an object with the second X-ray detector; determining an area of interest of the object based on the first image; and taking a second image of the area of interest with the first X-ray detector.

According to an embodiment, the method further comprises moving the first X-ray detector to a position suitable to take an image of the area of interest before taking the second image.

According to an embodiment, the method further comprises making a composite image by combining the first image and the second image.

BRIEF DESCRIPTION OF FIGURES

FIG. 7-FIG. 13 each schematically show a system comprising the X-ray detector described herein.

DETAILED DESCRIPTION

Figure 1:
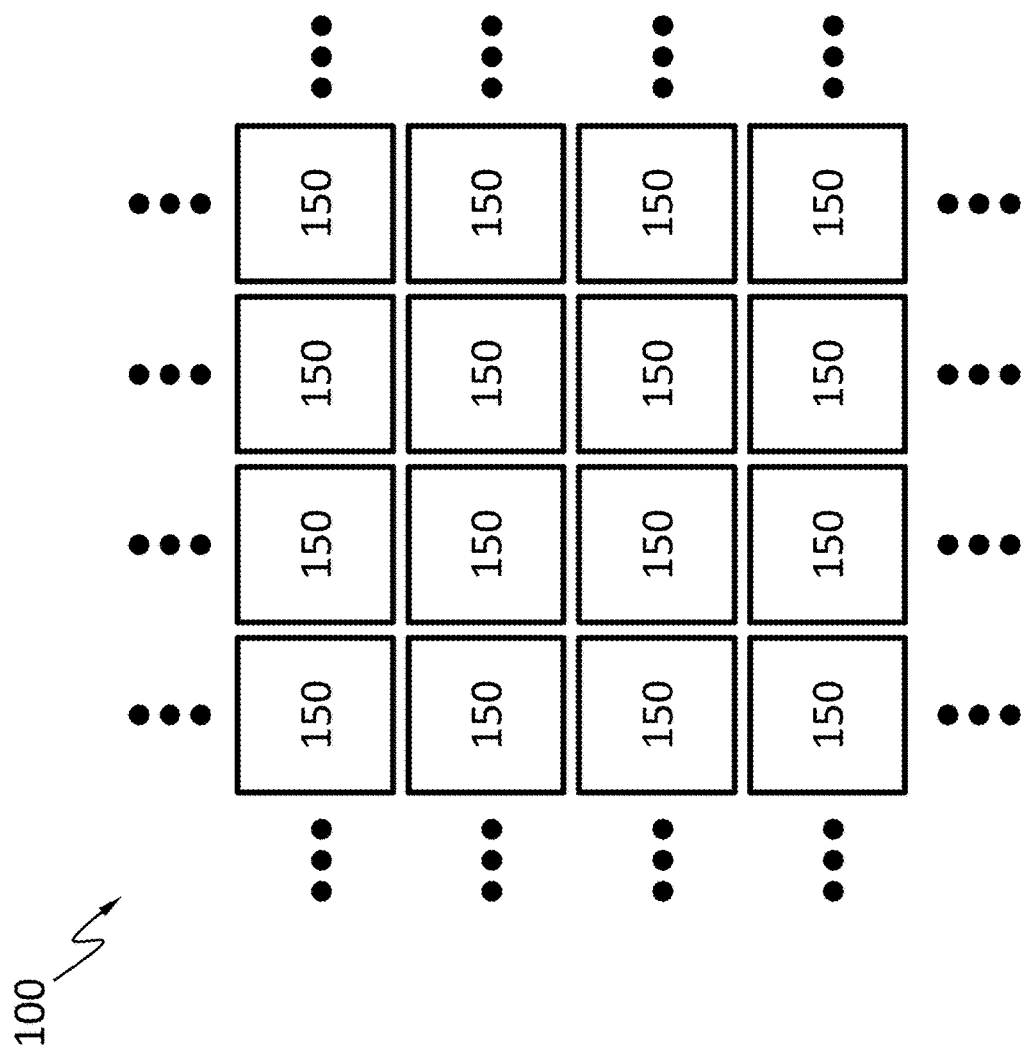
FIG. 1 schematically shows an X-ray detector, according to an embodiment.

FIG. 1 schematically shows an X-ray detector 100, as an example. The X-ray detector 100 has an array of pixels 150. The array may be a rectangular array, a honeycomb array, a hexagonal array or any other suitable array. Each pixel 150 is configured to detect radiation from a radiation source incident thereon and may be configured measure a characteristic (e.g., the energy of the particles, the wavelength, and the frequency) of the radiation. For example, each pixel 150 is configured to count numbers of photons incident thereon whose energy falls in a plurality of bins, within a period of time. All the pixels 150 may be configured to count the numbers of photons incident thereon within a plurality of bins of energy within the same period of time. Each pixel 150 may have its own analog-to-digital converter (ADC) configured to digitize an analog signal representing the energy of an incident photon into a digital signal. The pixels 150 may be configured to operate in parallel. For example, when one pixel 150 measures an incident photon, another pixel 150 may be waiting for a photon to arrive. The pixels 150 may not have to be individually addressable.

Figure 2A:
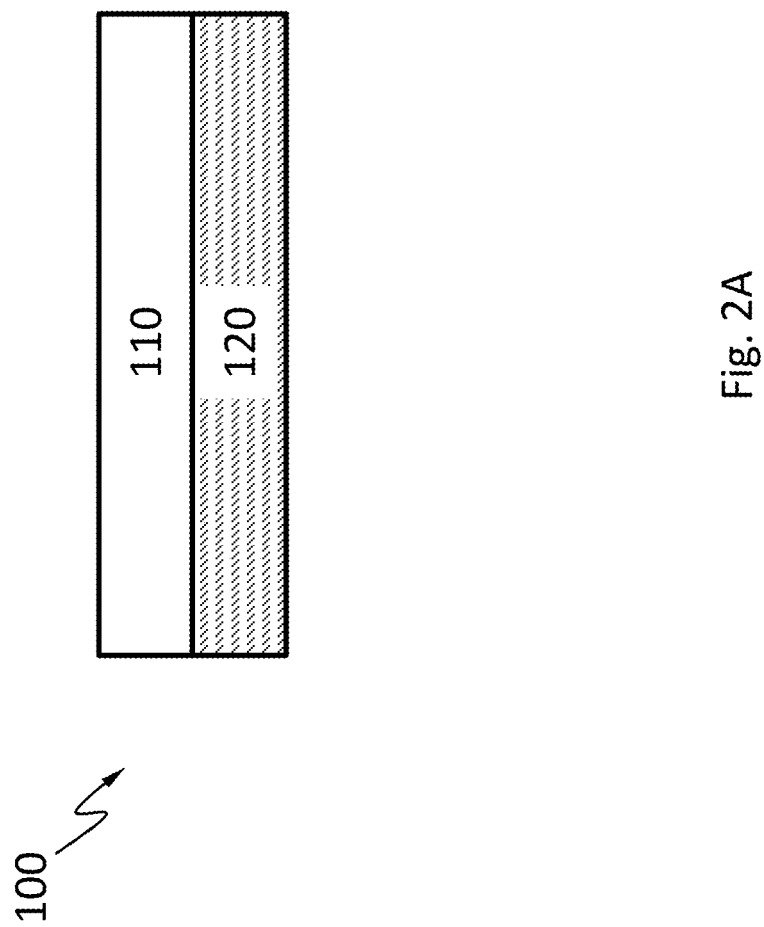
FIG. 2A schematically shows a cross-sectional view of the X-ray detector.

FIG. 2A schematically shows a cross-sectional view of the X-ray detector 100, according to an embodiment. The X-ray detector 100 may include a radiation absorption layer 110 and an electronics layer 120 (e.g., an ASIC) for processing or analyzing electrical signals incident radiation generates in the radiation absorption layer 110. The detector 100 may or may not include a scintillator. The radiation absorption layer 110 may include a semiconductor material such as, silicon, germanium, GaAs, CdTe, CdZnTe, or a combination thereof. The semiconductor may have a high mass attenuation coefficient for the radiation of interest.

Figure 2B:
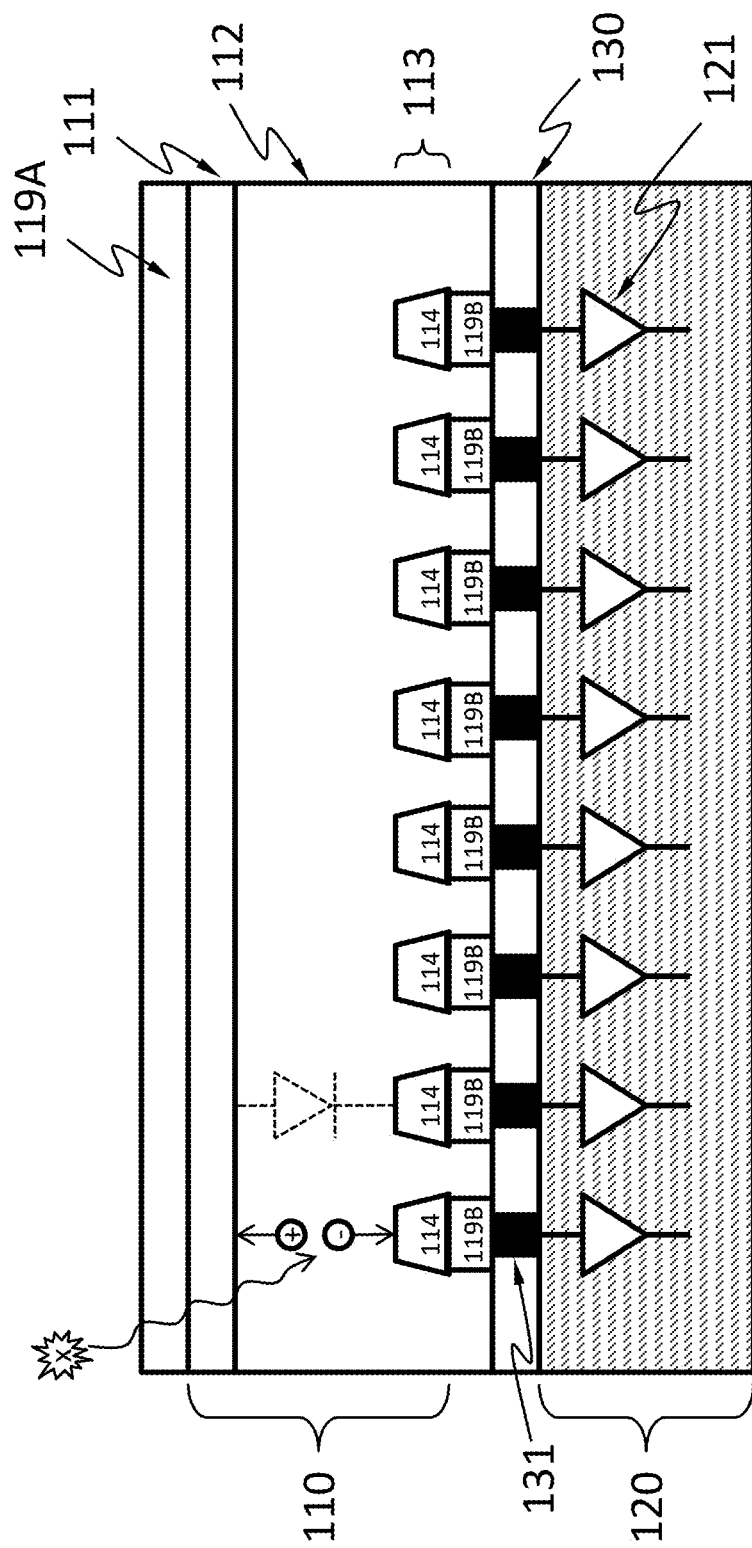
FIG. 2B schematically shows a detailed cross-sectional view of the X-ray detector.

As shown in a detailed cross-sectional view of the X-ray detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When radiation from the radiation source hits the radiation absorption layer 110 including diodes, the radiation photon may be absorbed and generate one or more charge carriers by a number of mechanisms. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel.

Figure 2C:
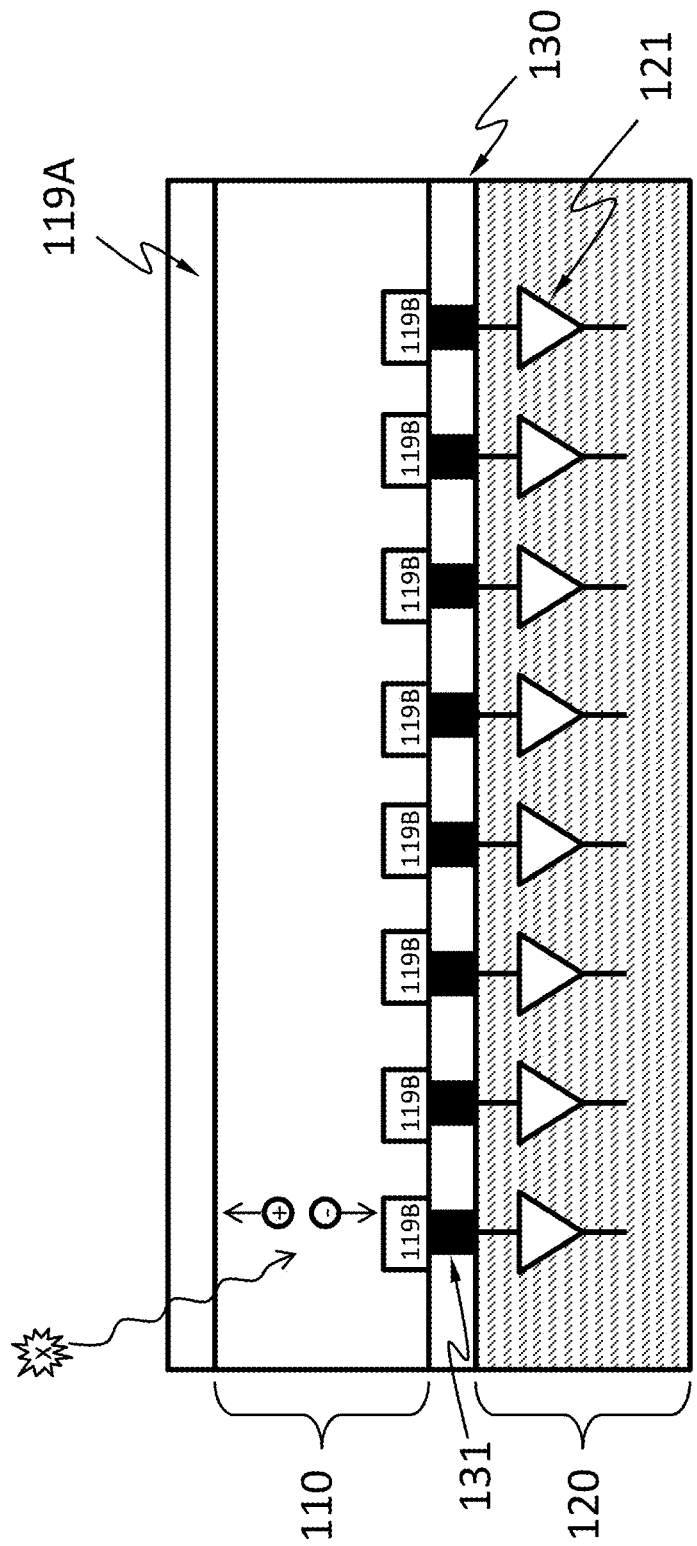
FIG. 2C schematically shows an alternative detailed cross-sectional view of the X-ray detector.

As shown in an alternative detailed cross-sectional view of the X-ray detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation of interest.

When the radiation hits the radiation absorption layer 110 including a resistor but not diodes, it may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single particle of the radiation are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by a particle of the radiation incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

The signals generated by the radiation incident on the radiation absorption layer 110 may be in a form of an electrical current. Likewise, the dark noise may also be in a form of an electrical current (e.g., a DC current flowing from the electric contacts 119B). If the current may be ascertained, the electrical current may be compensated for (e.g., diverted from) the electronic system 121.

Figure 3:
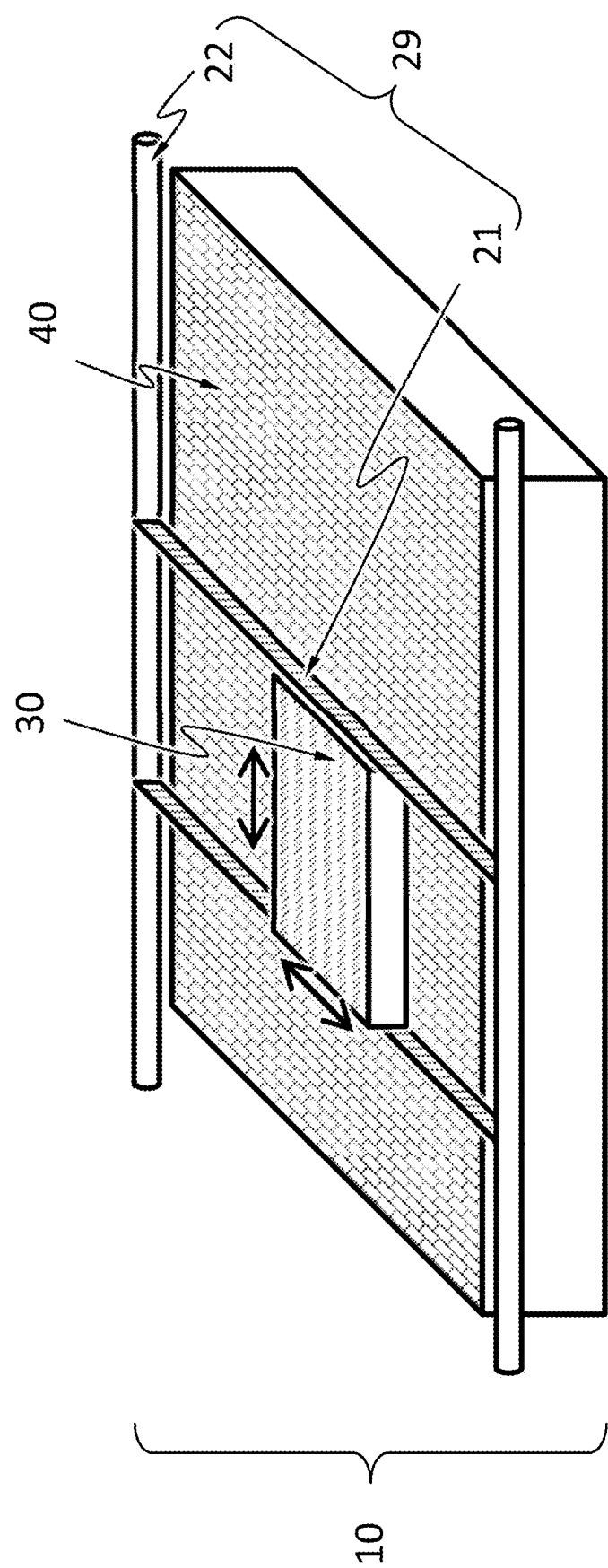
FIG. 3 schematically shows an X-ray detector comprising a first X-ray detector and a second X-ray detector, according to an embodiment.

According to embodiment, as schematically shown in FIG. 3, an X-ray imaging system 10 suitable for detecting x-ray comprises a first X-ray detector 30, and a second X-ray detector 40. The first X-ray detector 30 is configured to move relative to the second X-ray detector 40. A spatial resolution of the first X-ray detector 30 is higher than a spatial resolution of the second X-ray detector 40. The first X-ray detector 30 and the second X-ray detector 40 are each capable of forming an image. The first X-ray detector 30 generally may have a detection area that is smaller than a detection area of the second X-ray detector 40. As used herein, a detection area of an X-ray detector is the area thereof that is capable of detecting X-ray.

The first X-ray detector 30 may be any suitable X-ray detector, including but not limited to the X-ray detector 100 shown in FIG. 1 and FIG. 2A-FIG. 2C. For example, the first X-ray detector may count photons of X-ray incident thereon. For example, the first X-ray detector 30 may be pixelated. According to an embodiment, the first X-ray detector may comprise cadmium telluride (CdTe) or cadmium zinc telluride (CZT). According to an embodiment, the second X-ray detector comprises a scintillator. Semiconductors CdTe and CZT have emerged as the material of choice for room temperature detection of hard X-rays, as they provide high spatial and temporal resolution in imaging. One application of such X-ray detector with a first CZT detector is medical imaging in medical operations such as heart surgeries. According to an embodiment, the second X-ray detector may have a scintillator; alternatively the second X-ray detector may be a semiconductor X-ray detector capable of photo counting, but with a lower resolution than the first detector.

According to an embodiment, the first X-ray detector may be on top of the second X-ray detector in an overlay fashion. Alternatively, the first X-ray detector may be on a side of the second X-ray detector.

According to an embodiment, the X-ray imaging system 10 further comprises a special filter for the x-ray source, so that only the detection area corresponding to the first detector may receive enough x-ray dose, while the rest of the detection area may receive only reduced X-ray dose. Such X-ray imaging system 10 may reduce radiation dose received by the patient. According to an embodiment, the filter may have a rectangle hole in the middle to allow the X-ray to pass through, and the rectangle hole is aligned with the detection area corresponding to the first detector; the rest of the filter is made of copper of a predetermined thickness that may reduce the X-ray radiation dose.

According to an embodiment, a frame rate of the first X-ray detector 30 is higher than a frame rate of the second X-ray detector 40; such an X-ray imaging system 10 may work as a DSA detector. For example, the first X-ray detector 30 can work at 30 frame per second, while the second X-ray detector 40 only work at 10 frames per second.

According to an embodiment, the X-ray imaging system 10 further comprises an actuator 29 configured to move the first X-ray detector 30 relative to the second X-ray detector 40 in one or more directions; and at least one of the one or more directions is not perpendicular to an imaging plane of the second X-ray detector 40. As used herein, an imaging plane is the plane from which the detector takes image from. When the first X-ray detector and the second X-ray detector are used to take images from an object, the first X-ray detector is often used to take a high resolution image on an area of interest on the object, and the second X-ray detector is often used to take a low resolution background image on the overall object or a larger area of the object that comprises the area of interest. In such an example, the imaging planes of the first X-ray detector and the second X-ray detector are the same or are in close proximity, and the first X-ray detector is moved approximately parallel to the second X-ray detector.

According to an embodiment, the actuator comprises a material that has low X-ray absorption, and the material may be selected from a group consisting of aluminum, aluminum composite, carbon fiber and a combination thereof. Such material selection ensures the actuator is generally not shown in the X-ray imaging results. The actuator may be moved out of the view of the second X-ray detector.

According to an embodiment, as shown in FIG. 3, the actuator 29 comprises a first rail 21 and a second rail 22; the first X-ray detector 30 may slide along the first rail 21; and the first rail 21 may slide along the second rail 22 so that the first X-ray detector 30 is moved relative to the second X-ray detector 40. The first and second rails are not parallel. The first and second rails may be at an angle that is 90 degrees or not 90 degrees. The directions of the first and second rails may or may not be parallel to the edges of the second detector; therefore the directions of the edges of the first detector may or may not be parallel to the edges of the second detector.

Figure 4:
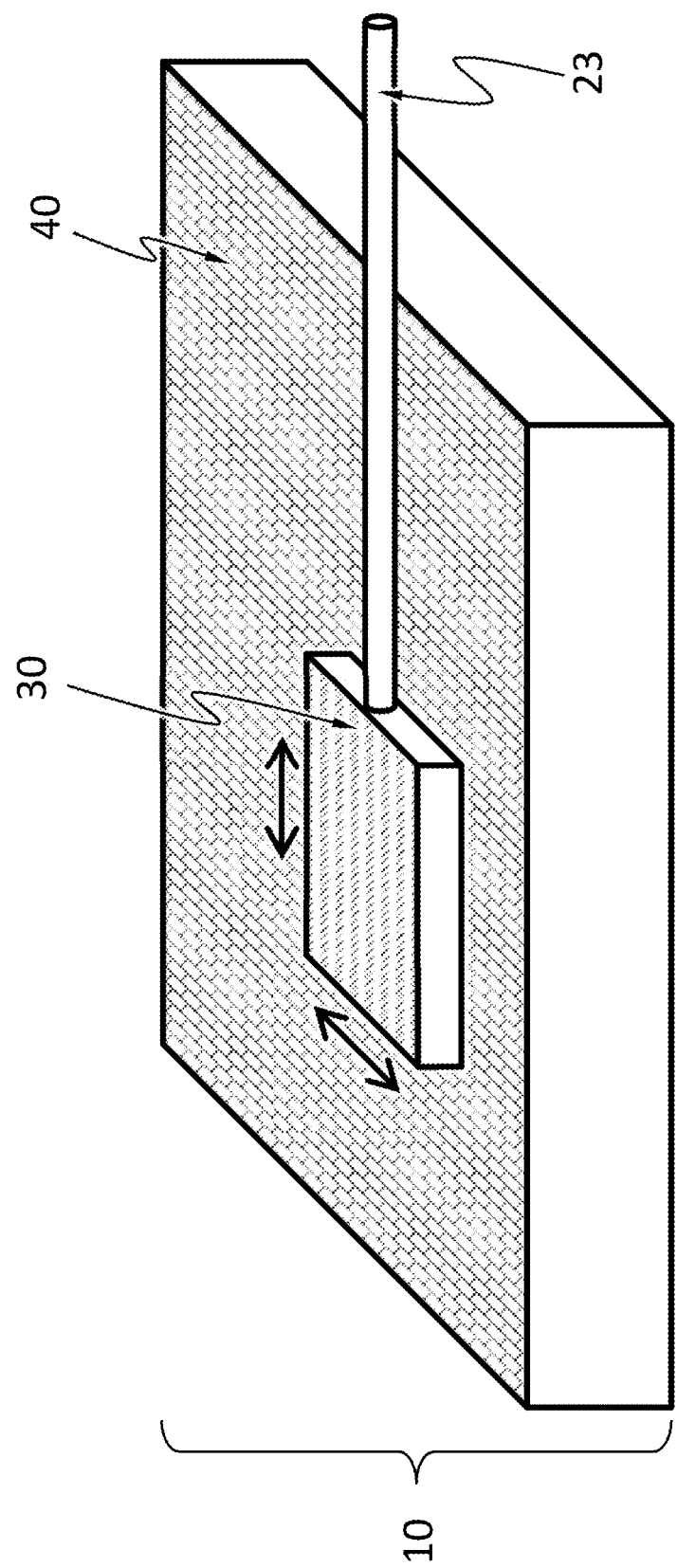
FIG. 4 schematically shows an X-ray detector comprising a first X-ray detector and a second X-ray detector, according to an embodiment.

According to an embodiment, as shown in FIG. 4, the actuator 29 comprises a robotic arm 23 that connects to the first X-ray detector 30; and when in use the robotic arm 23 moves the first X-ray detector 30 relative to the second X-ray detector 40 to an area of interest. The actuator 29 may have other forms that function to move the first X-ray detector relative to the second X-ray detector.

Figure 5:
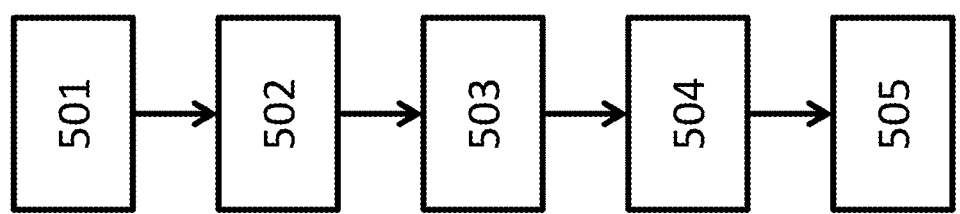
FIG. 5 schematically shows a method of using an X-ray detector comprising a first X-ray detector and a second X-ray detector, according to an embodiment.

The X-ray imaging system described above may be used in wide applications including but not limited to medical imaging. In an example schematically shown in FIG. 5, a first image of an object is taken with the second X-ray detector in procedure 501; an area of interest of the object is determined based on the first image in procedure 502; and a second image of the area of interest is taken with the first X-ray detector in procedure 504.

The first X-ray detector may be moved to a position suitable for taking an image of the area of interest in procedure 503, before taking the second image.

A composite image may be made by combining the first image and the second image in procedure 505.

The first X-ray detector may further comprise components, for example, as described below.

Figure 6A:
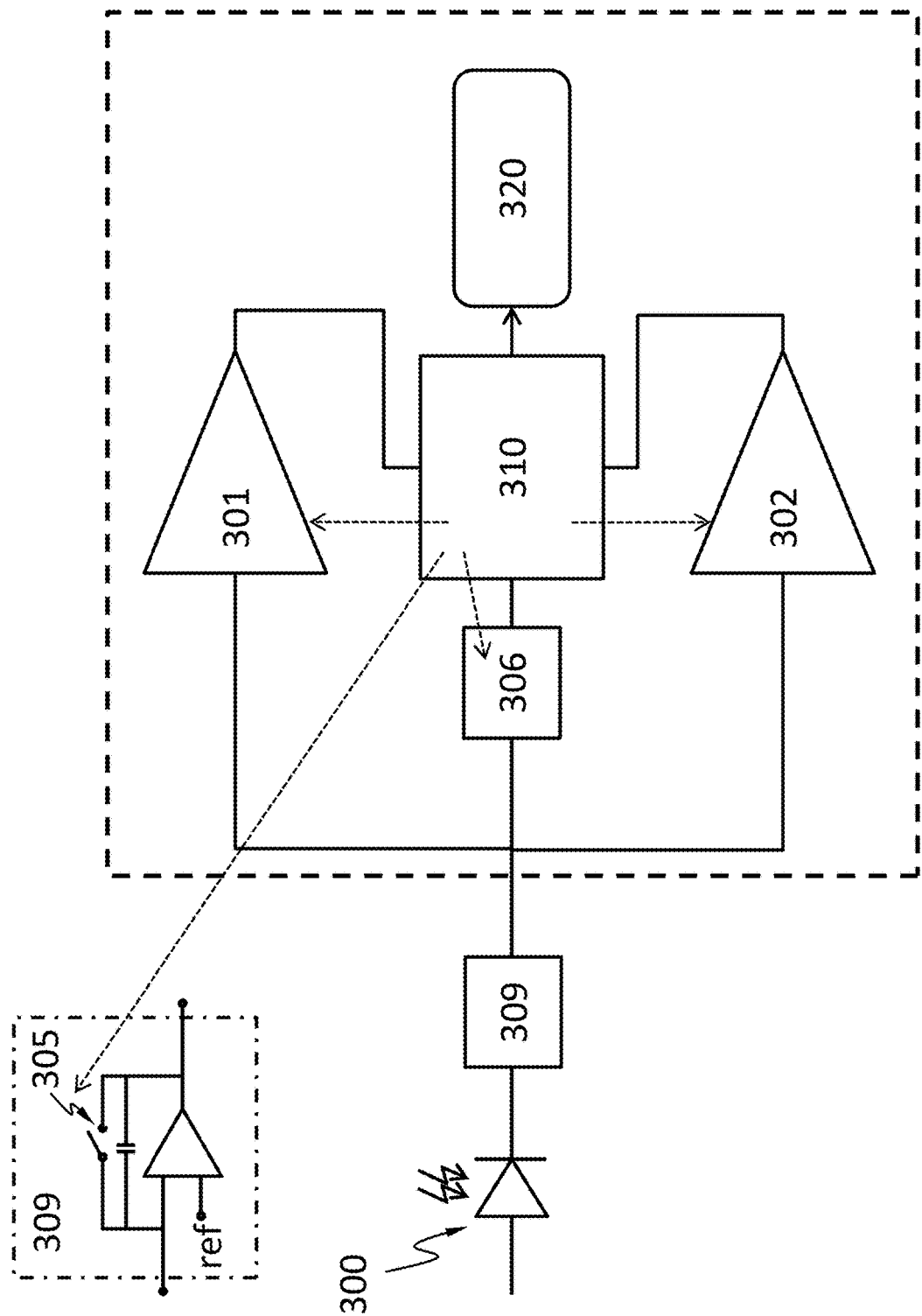
FIG. 6A and FIG. 6B each show a component diagram of an electronic system of the detector in FIG. 2B of FIG. 2C, according to an embodiment.
Figure 6B:
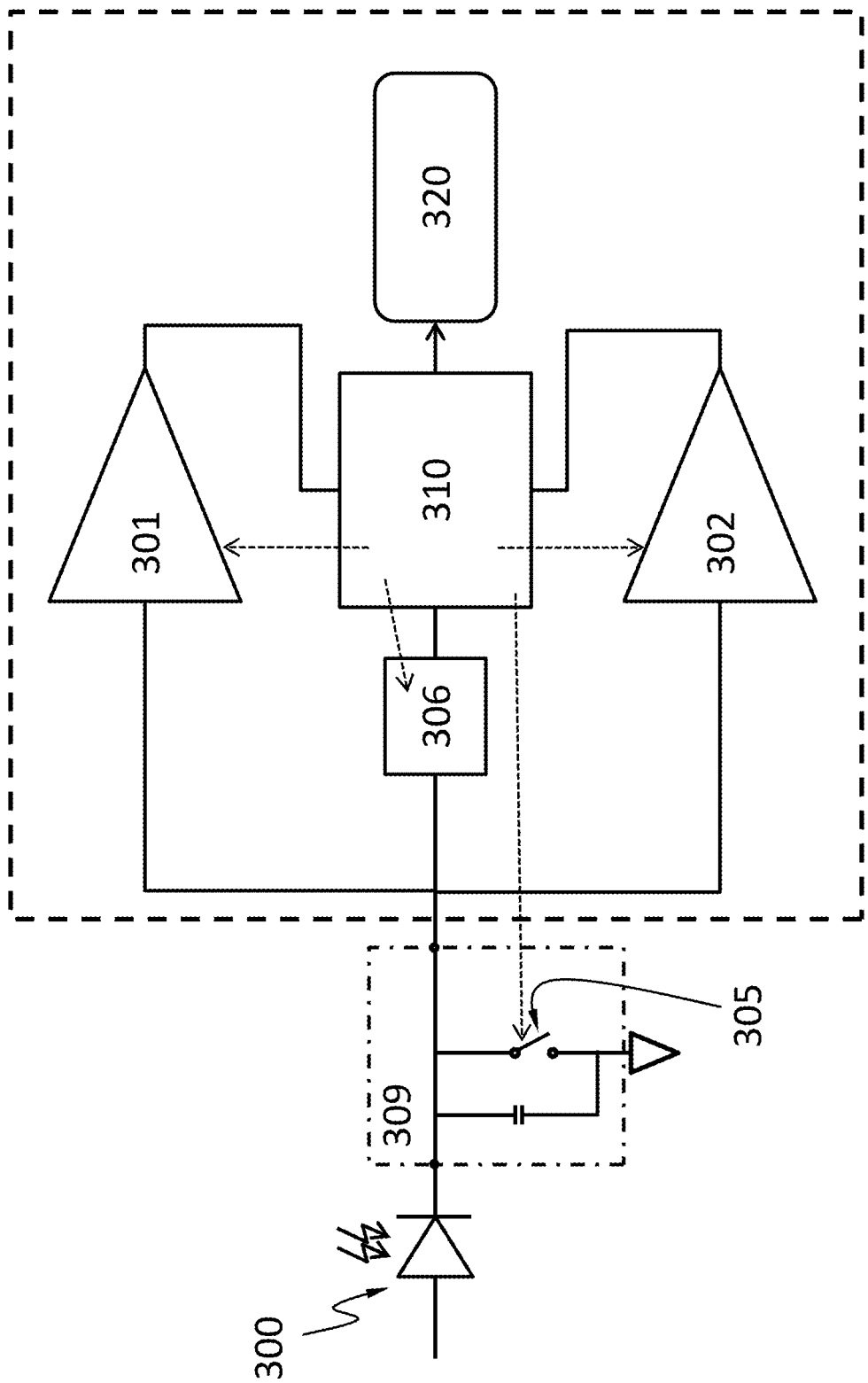

FIG. 6A and FIG. 6B each show a component diagram of the electronic system 121, according to an embodiment. The system 121 includes a capacitor module 309 electrically connected to an electrode of a diode 300 or an electrical contact, wherein the capacitor module is configured to collect charge carriers from the electrode. The capacitor module can include a capacitor and charge carriers from the electrode accumulate on the capacitor over a period of time ("integration period"). After the integration period has expired, the capacitor voltage is sampled and then reset by a reset switch. The capacitor module can include a capacitor directly connected to the electrode. The capacitor may be in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path.

In addition the capacitor module 309, which includes the current sourcing module 388, the electronic system 121 may further include a first voltage comparator 301, a second voltage comparator 302, a counter 320, a switch 305, a voltmeter 306 and a controller 310, as shown in FIG. 6A and FIG. 6B.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{if } x \geq 0 \\ -x, \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

The controller 310 may be configured to control the current sourcing module 388. For example, the controller 310 may change the magnitude of compensation for the dark noise by controlling the current sourcing module 388.

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 7:
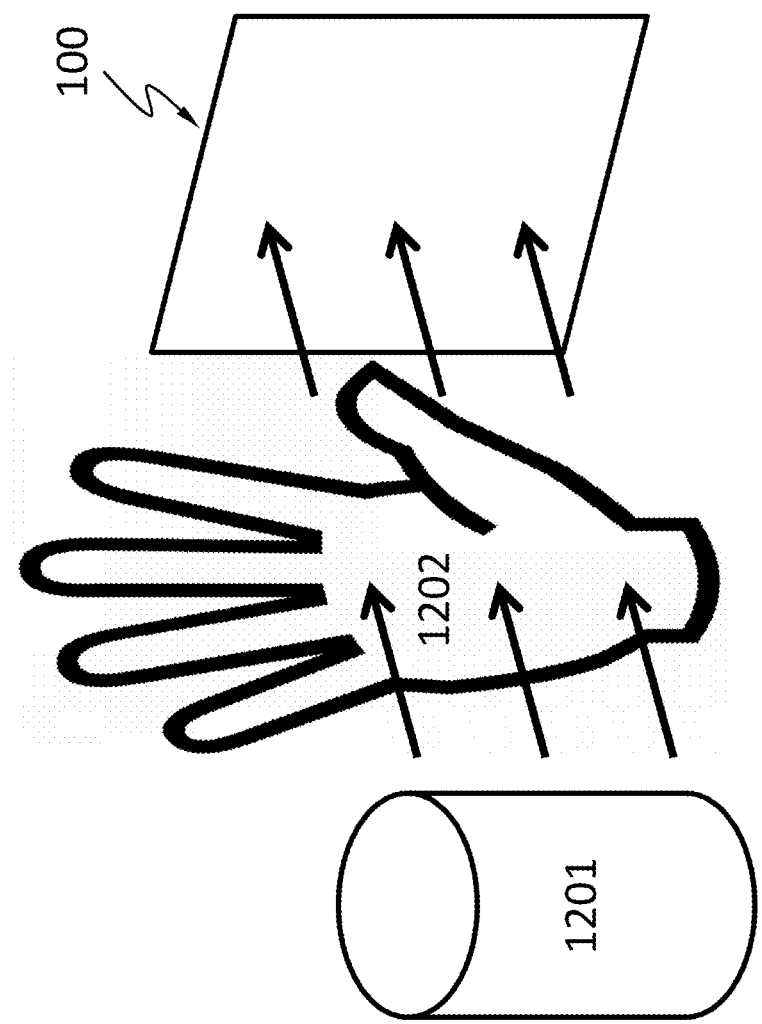

FIG. 7 schematically shows a system comprising the X-ray detector 100 described herein. The system may be used for medical imaging such as chest X-ray radiography, abdominal X-ray radiography, etc. The system comprises a pulsed radiation source 1201 that emits X-ray. X-ray emitted from the pulsed radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the X-ray detector 100. The X-ray detector 100 forms an image by detecting the intensity distribution of the X-ray.

Figure 8:
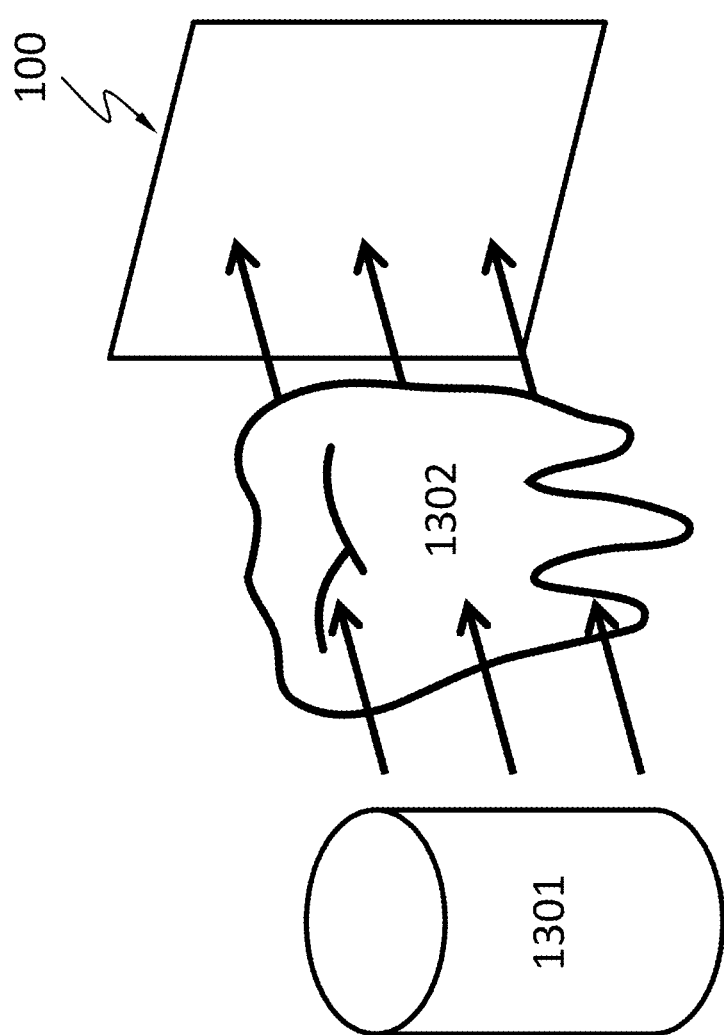

FIG. 8 schematically shows a system comprising the X-ray detector 100 described herein. The system may be used for medical imaging such as dental X-ray radiography. The system comprises a pulsed radiation source 1301 that emits X-ray. X-ray emitted from the pulsed radiation source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the X-ray detector 100. The X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 9:
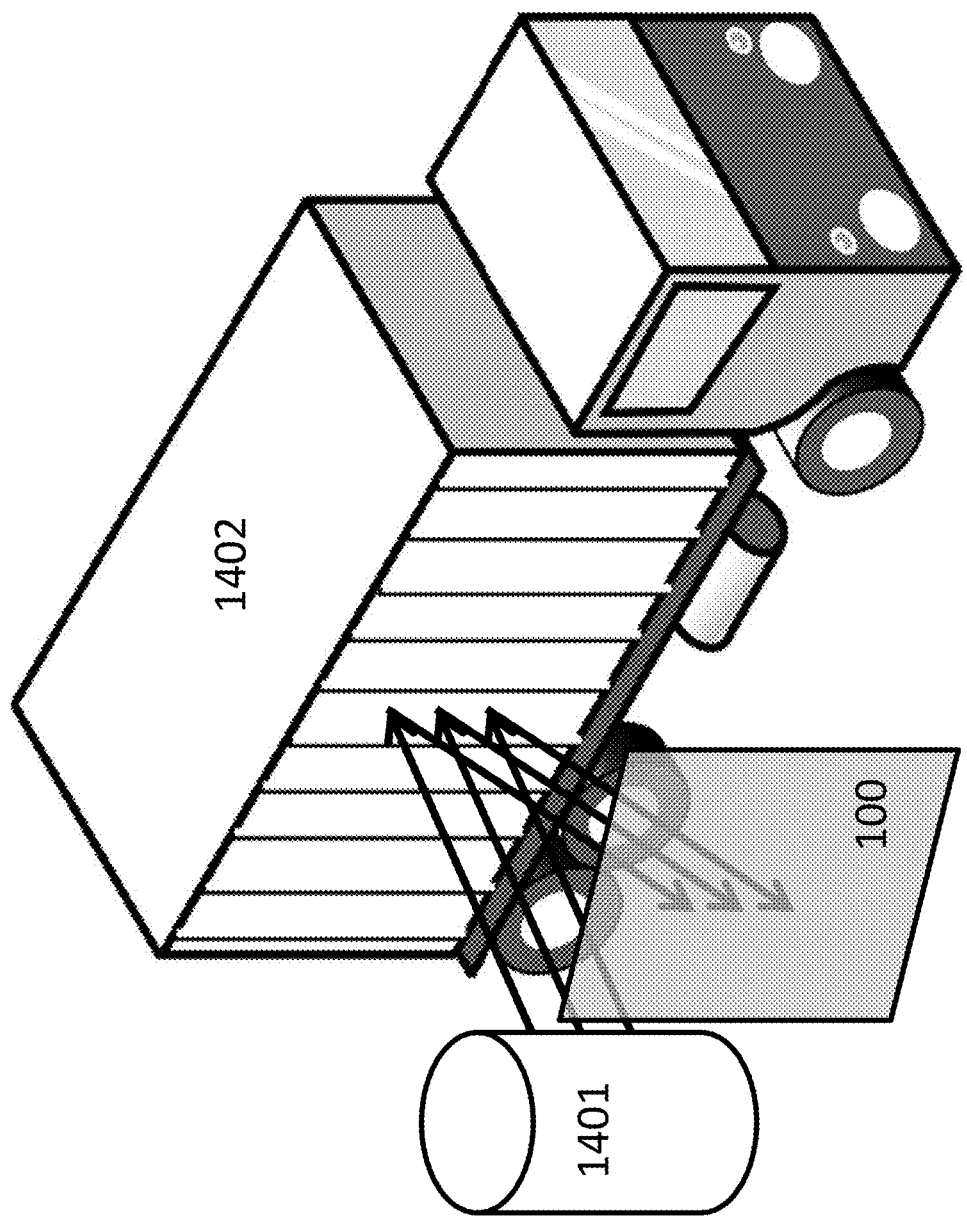

FIG. 9 schematically shows a cargo scanning or non-intrusive inspection (NII) system comprising the X-ray detector 100 described herein. The system may be used for inspecting and identifying goods in transportation systems such as shipping containers, vehicles, ships, luggage, etc. The system comprises a pulsed radiation source 1401. Radiation emitted from the pulsed radiation source 1401 may backscatter from an object 1402 (e.g., shipping containers, vehicles, ships, etc.) and be projected to the X-ray detector 100. Different internal structures of the object 1402 may backscatter the radiation differently. The X-ray detector 100 forms an image by detecting the intensity distribution of the backscattered radiation and/or energies of the backscattered radiation.

Figure 10:
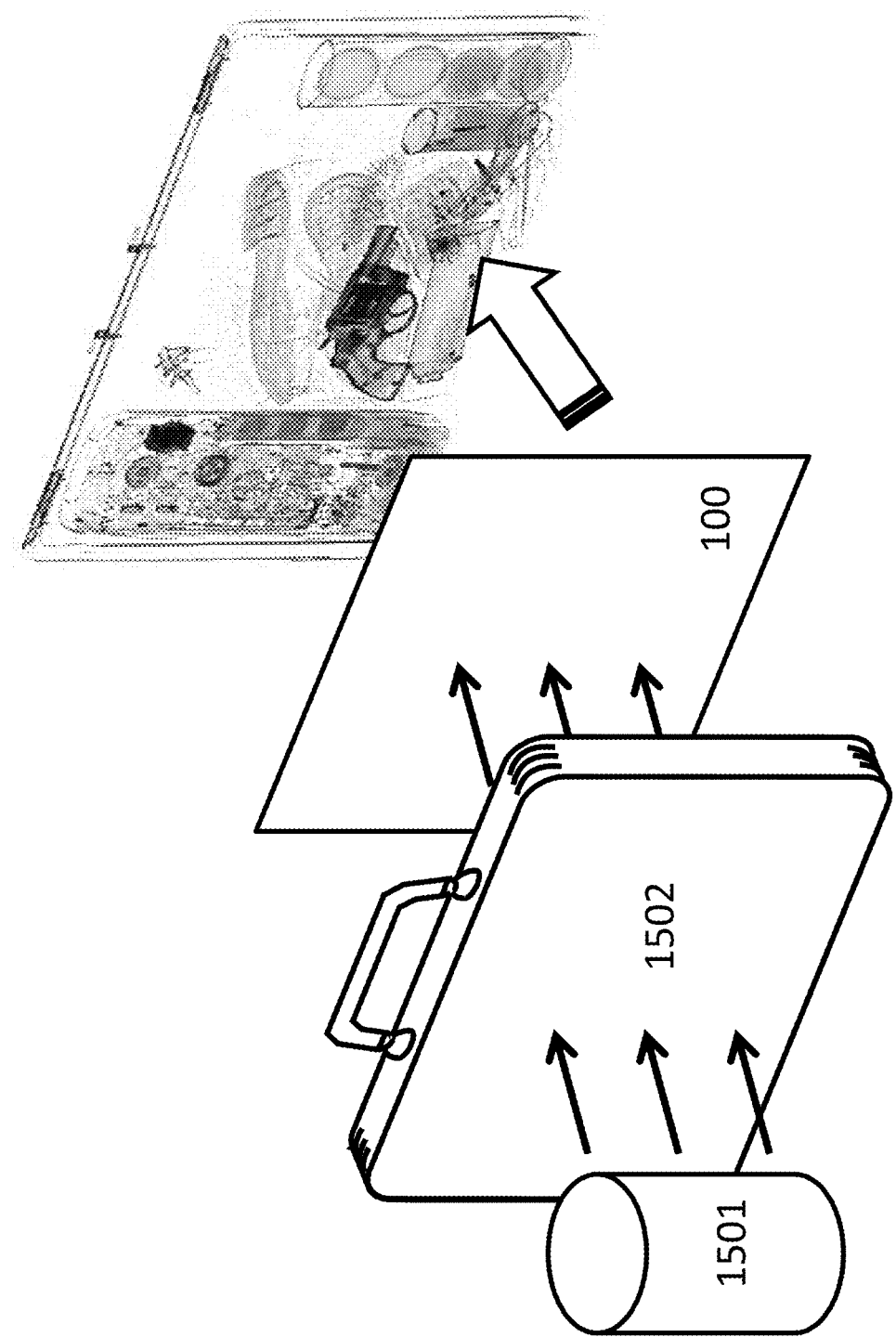

FIG. 10 schematically shows another cargo scanning or non-intrusive inspection (NII) system comprising the X-ray detector 100 described herein. The system may be used for luggage screening at public transportation stations and airports. The system comprises a pulsed radiation source 1501 that emits X-ray. X-ray emitted from the pulsed radiation source 1501 may penetrate a piece of luggage 1502, be differently attenuated by the contents of the luggage, and projected to the X-ray detector 100. The X-ray detector 100 forms an image by detecting the intensity distribution of the transmitted X-ray. The system may reveal contents of luggage and identify items forbidden on public transportation, such as firearms, narcotics, edged weapons, flammables.

Figure 11:
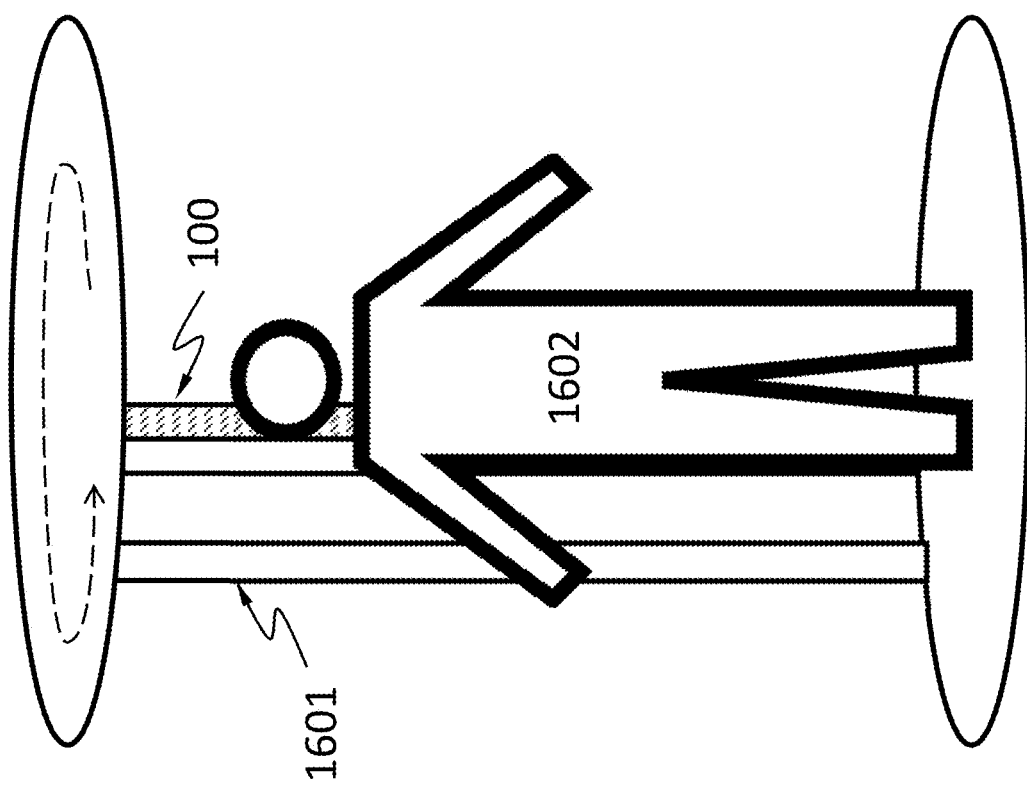

FIG. 11 schematically shows a full-body scanner system comprising the X-ray detector 100 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the X-ray detector 100. The objects and the human body may backscatter the radiation differently. The X-ray detector 100 forms an image by detecting the intensity distribution of the backscattered radiation. The X-ray detector 100 and the pulsed radiation source 1601 may be configured to scan the human in a linear or rotational direction.

FIG. 12 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the X-ray detector 100 described herein and a pulsed radiation source 1701 that emits X-ray. The X-ray detector 100 and the pulsed radiation source 1701 may be configured to rotate synchronously along one or more circular or spiral paths.

FIG. 13 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the X-ray detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the X-ray detector 100.

The X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this X-ray detector 100 in place of a photographic plate, a photographic film, a PSP plate, an X-ray image intensifier, a scintillator, or an X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An X-ray imaging system suitable for detecting x-ray, comprising:
   a first X-ray detector, and a second X-ray detector;
   wherein the first X-ray detector is configured to move relative to the second X-ray detector;
   wherein a spatial resolution of the first X-ray detector is higher than a spatial resolution of the second X-ray detector;

wherein a detection area of the first X-ray detector is smaller than a detection area of the second X-ray detector;
wherein the first X-ray detector comprises:
an X-ray absorption layer comprising an electrode;
a first voltage comparator configured to compare a voltage of the electrode to a first threshold;
a second voltage comparator configured to compare the voltage to a second threshold;
a counter configured to register a number of X-ray photons absorbed by the X-ray absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold.

2. The X-ray imaging system of claim 1, wherein the first X-ray detector and the second X-ray detector are each capable of forming an image.

3. The X-ray imaging system of claim 1, wherein the first X-ray detector is configured to count photons of X-ray incident thereon.

4. The X-ray imaging system of claim 1, wherein the first X-ray detector is pixelated.

5. The X-ray imaging system of claim 1, wherein the first X-ray detector comprises cadmium telluride (CdTe) or cadmium zinc telluride (CZT).

6. The X-ray imaging system of claim 1, wherein the second X-ray detector comprises a scintillator.

7. The X-ray imaging system of claim 1, comprising an actuator configured to move the first X-ray detector relative to the second X-ray detector in one or more directions; wherein one of the one or more directions is not perpendicular to an imaging plane of the second X-ray detector.

8. The X-ray imaging system of claim 7, wherein the actuator comprises a material that is selected from a group consisting of aluminum, aluminum composite, carbon fiber and a combination thereof.

9. The X-ray imaging system of claim 7, wherein the actuator comprises a robotic arm.

10. The X-ray imaging system of claim 7, wherein the actuator comprises a first rail and a second rail; wherein the first X-ray detector is configured to slide along the first rail; and wherein the first rail is configured to slide along the second rail, wherein the first and second rails are not parallel.

11. The X-ray imaging system of claim 1, wherein the first X-ray detector further comprises a capacitor module electrically connected to the electrode, wherein the capacitor module is configured to collect charge carriers from the electrode.

12. The X-ray imaging system of claim 1, wherein the controller is configured to activate the second voltage comparator at a beginning or expiration of the time delay.

13. The X-ray imaging system of claim 1, wherein the first X-ray detector further comprises a voltmeter, wherein the controller is configured to cause the voltmeter to measure the voltage upon expiration of the time delay.

14. The X-ray imaging system of claim 1, wherein the controller is configured to determine an X-ray photon energy based on a value of the voltage measured upon expiration of the time delay.

15. The X-ray imaging system of claim 1, wherein the controller is configured to connect the electrode to an electrical ground.

16. The X-ray imaging system of claim 1, wherein a rate of change of the voltage is substantially zero at expiration of the time delay.

17. The X-ray imaging system of claim 1, wherein a rate of change of the voltage is substantially non-zero at expiration of the time delay.

18. The X-ray imaging system of claim 1, wherein the X-ray absorption layer comprises a diode.

19. The X-ray imaging system of claim 1, wherein the X-ray absorption layer comprises silicon, germanium, GaAs, CdTe, CdZnTe, or a combination thereof.

20. The X-ray imaging system of claim 1, wherein the first X-ray detector does not comprise a scintillator.

21. A system comprising the X-ray imaging system of claim 1 and an X-ray source, wherein the system is configured to perform X-ray radiography on human chest or abdomen.

22. A system comprising the X-ray imaging system of claim 1 and an X-ray source, wherein the system is configured to perform X-ray radiography on human mouth.

23. A cargo scanning or non-intrusive inspection (NII) system, comprising the X-ray imaging system of claim 1 and an X-ray source, wherein the cargo scanning or non-intrusive inspection (NII) system is configured to form an image using backscattered X-ray.

24. A cargo scanning or non-intrusive inspection (NII) system, comprising the X-ray imaging system of claim 1 and an X-ray source, wherein the cargo scanning or non-intrusive inspection (NII) system is configured to form an image using X-ray transmitted through an object inspected.

25. A full-body scanner system comprising the X-ray imaging system of claim 1 and an X-ray source.

26. An X-ray computed tomography (X-ray CT) system comprising the X-ray imaging system of claim 1 and an X-ray source.

27. An electron microscope comprising the X-ray imaging system of claim 1, an electron source and an electronic optical system.

28. A system comprising the X-ray imaging system of claim 1, wherein the system is an X-ray telescope, or an X-ray microscopy, or wherein the system is configured to perform mammography, industrial defect detection, microradiography, casting inspection, weld inspection, or digital subtraction angiography.

29. A method of X-ray imaging using an X-ray imaging system, wherein the X-ray imaging system comprises:
a first X-ray detector, and a second X-ray detector;
wherein the first X-ray detector is configured to move relative to the second X-ray detector;
wherein a spatial resolution of the first X-ray detector is higher than a spatial resolution of the second X-ray detector;
wherein a detection area of the first X-ray detector is smaller than a detection area of the second X-ray detector;
wherein the first X-ray detector comprises:
an X-ray absorption layer comprising an electrode;
a first voltage comparator configured to compare a voltage of the electrode to a first threshold;

a second voltage comparator configured to compare the voltage to a second threshold;
a counter configured to register a number of X-ray photons absorbed by the X-ray absorption layer;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold;
the method comprising:
   taking a first image of an object with the second X-ray detector;
   determining an area of interest of the object based on the first image; and
   taking a second image of the area of interest with the first X-ray detector.

30. The method of claim 29, comprising:
moving the first X-ray detector to a position suitable to take an image of the area of interest before taking the second image.

31. The method of claim 29, comprising:
making a composite image by combining the first image and the second image.

32. The X-ray imaging system of claim 29, wherein the first X-ray detector is configured to overlay the second X-ray detector while the first X-ray detector moves.

33. The method of claim 29, further comprising moving the first X-ray detector to the area of interest, wherein the first X-ray detector overlays the second X-ray detector while the first X-ray detector is moved.

* * * * *